United States Patent [19]

Farb et al.

[11] Patent Number: 4,758,657
[45] Date of Patent: Jul. 19, 1988

[54] METHOD OF PURIFYING FACTOR VIII:C

[75] Inventors: David L. Farb, Lake Ridge, Va.; Ricardo H. Landaburu, Rye Town, N.Y.

[73] Assignee: Armour Pharmaceutical Company, Fort Washington, Pa.

[21] Appl. No.: 753,822

[22] Filed: Jul. 11, 1985

[51] Int. Cl.$^4$ .................. C07K 3/20; A61K 35/14; A61K 37/02
[52] U.S. Cl. ............................. 530/383; 530/413; 530/417; 424/101
[58] Field of Search .............. 424/101; 530/383, 413, 530/417

[56] References Cited

U.S. PATENT DOCUMENTS

| | | | |
|---|---|---|---|
| 4,069,216 | 1/1978 | Shanbrom | 424/101 |
| 4,314,997 | 2/1982 | Shanbrom | 424/101 |
| 4,361,509 | 11/1982 | Zimmerman | 424/101 |
| 4,673,733 | 6/1987 | Chandra et al. | 530/383 |

OTHER PUBLICATIONS

Morgenthaler, *Thromb. Haemostas.*, 47(2), 124–127, 1982.

*Primary Examiner*—J. R. Brown
*Assistant Examiner*—Jacqueline M. Stone

[57] ABSTRACT

Disclosed is a process for purifying Factor VIII:C in high yield and potency from source material containing Factor VIII:C, Factor VIII:R and other plasma proteins and factors comprising the steps of: adsorbing Factor VIII:C onto a hydrophobic interaction matrix, separating unwanted proteins from Factor VIII:C and eluting Factor VIII:C by a solution containing a surface active agent.

5 Claims, No Drawings

METHOD OF PURIFYING FACTOR VIII:C

BACKGROUND OF THE INVENTION

1. Field of the Invention

This invention relates to a method of purifying Factor VIII:C which is useful for therapeutic administration to patients having hemophilia.

Hemostatis, the biochemistry of blood coagulation, is an extremely complex and as yet not completely understood phenomena whereby normal whole blood and body tissue prevent an excess loss of blood from a ruptured blood vessel. The total mechanism of blood coagulation is affected through the coordinated interaction of biochemical substances contained in three basic physiologic systems; namely, extravascular tissue such as subcutaneous tissue, muscle tissue, and skin; the blood vessel wall; and intravascular components, including blood plasma proteins, blood plasma factors, and platelets.

A great deal of medical research into blood clotting diseases has been directed towards finding an acceptable treatment for hemophilia, a genetically induced disease characterized by the loss of clottability of otherwise normal whole blood. Although the precise cause of hemophilia is not known, one of the most popular theories suggests that it may be because of the absence of or a greatly inhibited presence of the active form of antihemophilic factor (hereinafter AHF) in otherwise normal plasma from whole blood. At present, although hemophilia cannot be cured, it can often be treated therapeutically by the administration of AHF to an AHF-deficient individual. The administered AHF is derived from blood obtained from a normal and healthy donor. AHF is administered either by the transfusion of whole blood or blood plasma, or by the infusion of AHF plasma protein concentrate which has been extracted from the plasma of normal human whole blood.

When whole blood or blood plasma transfusions are used to relieve a hemophiliac, one must exercise great care to select reasonably fresh blood or plasma because the biologic activity of AHF is extremely labile upon storage under normal conditions. Even laboratory techniques, such as lyophilization and cryogenic preservation, will not prevent substantial loss of biologic activity of AHF over time. Another major disadvantage of whole blood or blood plasma transfusions is that they can introduce unwanted proteinaceous and nonproteinaceous material in the recipient's blood stream, often causing allergic reactions to sensitive patients, viral infections such as hepatitis, or hypervolumetric reactions to those persons who require extensive amounts of AHF to initiate clotting.

Another method of therapeutic technique, namely, i.v. administration of AHF plasma concentrate, is presently being used extensively. These concentrates are being developed primarily to circumvent the aforementioned troublesome and often times dangerous side effects caused by whole blood or plasma transfusions.

Essentially, AHF plasma concentrate might be characterized as AHF-rich blood plasma extracts from which some blood plasma proteins, such as the gamma globulins, most other blood plasma factors, and many inorganic chemicals have been removed. However, even currently available AHF-rich blood plasma concentrates may contain impurities which can cause deleterious effects when administered to man so that a need for a purer, more therapeutically acceptable AHF plasma concentrate still exists.

AHF in its natural form as obtained from plasma consists of aggregates of two molecular entities, which are termed Factor VIII:R and Factor VIII:C. Factor VIII:C is biologically active in correcting the coagulation defect of Hemophilia A. Factor VIII:R, also known as Factor VIII:WF (von Willebrand Factor), is biologically active in correcting the coagulation defect of von Willebrand's disease, a disorder of platelet aggregation. During plasma fractionations designed to generate AHF rich extracts, Factor VIII:C and Factor VIII:R usually remain closely associated in a high molecular weight complex. Nevertheless, dissociation occurs in buffers containing high concentrations of calcium chloride, or sodium chloride at low pH values.

These conditions for dissociation are used in conjunction with chromatography of AHF plasma concentrates on aminohexyl-sepharose, quaternary aminoethyl-sepharose, or polyelectrolytes to separately elute Factor VIII:C and Factor VIII:R, often with reduced contamination by other plasma proteins. It is highly desirable to be able to purify Factor VIII:C with respect to Factor VIII:R and the other plasma proteins with which Factor VIII:C is normally found in order to provide antihemophilic therapy without risks of antigenic or viral side effects.

The present invention is directed to a method for obtaining highly purified Factor VIII:C having high specific activity for initiating clot formation intended to be used therapeutically to correct a clinical defect known as severe hemophilia A.

2. Description of the Prior Art

Various protein concentrates are known to contain Factor VIII:C activity, including human and animal plasma, such as described in U.S. Pat. No. 4,210,580 and extracts from cell cultures which have been genetically engineered to contain Factor VIII:C, such as described by Wood, et al, in *Nature*, Vol. 312, pp 330–336 (1984). Protein concentrates containing Factor VIII:C activity can be produced from the material referred to hereinabove by a variety of methods. Crude Factor VIII:C concentrates typically have potencies of 10 to 20 units per ml and purities of 1 to 5 units per mg.

Previously known processes for purifying Factor VIII:C introduce losses of yield and/or purity which up to now have been tolerated. The present invention achieves higher levels of purification and yield, without deactivation, in a manner which is not suggested by the prior art.

D. E. G. Austen, "The Chromatographic Separation of Factor VIII on Aminohexyl Sepharose", in *British Journal of Hematology*, 1979, (43) 669–674, described a chromatographic separation process in which human or porcine Factor VIII concentrate was passed through a column of 6-amino-n-hexyl-substituted agarose. The column and all eluting solutions were at a pH of 5.5. A high degree of separation of Factor VIII:C from Factor VIII:R, and a high degree of purification of Factor VIII:C from other proteins, were obtained. However, the total recovery of human Factor VIII:C was only 35–40%, and for porcine Factor VIII:C was only 24–30%. The authors indicate that more acidic pH values in the buffers (down to a pH of about 5.2) favor higher purification of Factor VIII:C, and they purposely chose the pH of 5.5 in order to have as acidic an environment as possible without suffering too low a yield.

Several recent publications have continued to insist on maintaining an acid pH in the chromatographic column. Morgenthaler, "Chromatography of Antihemophilic Factor on Diaminoalkane- and Aminoalkane-Derivatized Sepharose", *Thromb. Haemostas.* 47(2) 124-127 (1982), found that when AHF was chromatographed on Sepharose CL-2B agarose gel at pH values of 6.0, 6.5 and 7.0, no significant separation of Factors VIII:C and VIII:R could be obtained. Chromatography of AHF at a pH of 5.5 produced a very marked separation between Factors VIII:C and VIII:R. An even more recent paper, Faure, et al., "Improved buffer for the chromatographic separation of Factor VIII coagulent," *J. Chromatography* 257 (1983), 387-391, retains the pH value of 5.5 indicated by Austen and attempts to improve the performance of that chromatographic procedure by adding compounds to the buffers.

Factor VIII:C has been purified from crude AHF using a column at a pH closer to neutral only in the instance in which Factor VIII:R is employed to form a reversible complex with Factor VIII:C. The Factor VIII:C is then eluted in the presence of a neutral aqueous buffer containing at least 0.2M calcium chloride. Specifically, in U.S. Pat. No. 4,361,509, Zimmerman, et al. employ a column bearing monoclonal antibodies to Factor VIII:R to recover a dilute solution of Factor VIII:C that has been ultrapurified free of most Factor VIII:R.

The solution of ultrapurified Factor VIII:C obtained from either of the above techniques can be concentrated at a neutral pH around 6.8 using selected columns of diaminoalkane or aminoalkane derivatized agarose.

For diaminoalkane agarose, such as aminohexyl agarose, the salt concentration of the ultrapure Factor VIII:C solution must first be lowered to around 0.05M for efficient binding. The factor VIII:C is then eluted from the column with a buffer containing high concentrations of calcium chloride or sodium chloride at a neutral pH.

One type of aminoalkane derivatized agarose, butyl agarose, has also been used to concentrate ultrapurified Factor VIII:C solution following a similar manipulation of salt concentrations.

Other types of aminoalkane derivatized agarose such as pentyl-, hexyl-, heptyl-, and octyl-agarose as well as phenyl-agarose are generally known as hydrophobic interaction matrix.

Ultrapurified Factor VIII:C has been shown in the prior art to bind to each of the hydrophobic interaction matrix, however no active material has been recovered following elution with the salt solutions typically used by those skilled in the art. Recovery to a large degree is determined by the affinity of AHF to the hydrophobic interaction matrix from which AHF is difficult to separate by the use of salt solutions with various salt concentrations.

We have now discovered that the use of certain surface active agents in the elution buffer results in an effective recovery of AHF activity from hydrophobic interaction matrix.

SUMMARY OF THE INVENTION

The present invention is directed to a process for purifying Factor VIII:C in high yield and potency from source material containing Factor VIII:C, Factor VIII:R and other plasma proteins and factors, comprising:

(a) preparing an aqueous solution of said source material;

(b) adjusting the pH of said aqueous solution to 6.0 to 8.0;

(c) adding a neutral salt in a sufficient amount to make the solution 0.1 to 2M;

(d) adsorbing Factor VIII:C and foreign proteins onto a hydrophobic interaction matrix;

(e) eluting the foreign proteins from the hydrophobic interaction matrix by washing with an aqueous solution having a pH of 6.0 to 8.0 and containing 0.1 to 0.5M $CaCl_2$ and 0.1 to 40% w/w ethylene glycol;

(f) further washing the hydrophobic interaction matrix with an aqueous solution having a pH of 6.2 to 7.2 and containing 0.01 to 0.6M NaCl, 0.01 to 0.2M glycine, 0.001 to 0.020M $CaCl_2$ and 0.001 to 0.020M histidine; and (g) eluting Factor VIII:C by washing said hydrophobic interaction matrix with a water solution of 0.1 to 1% w/w of a surface active agent.

DETAILED DESCRIPTION OF THE INVENTION

Source material suitable for use in this invention includes any material containing Factor VIII:C with one or more other plasma proteins. Particular examples are materials which contain Factor VIII, i.e. the complex of Factors VIII:C and VIII:R, such as plasma, commercial Factor VIII concentrates, and cryoprecipitate obtained from plasma, as well as product fractions and otherwise discarded side fractions from the well-known Cohn fractionation process. Human-source material, as well as bovine and porcine, can be treated. Proteins besides Factor VIII:R that can be present include fibrinogen, fibronectin, and albumin.

When cryoprecipitate is the starting material, it should be reconstituted in an aqueous solution in the manner known generally to those skilled in this art, but observing the pH adjustment to 6.0 to 8.0. Plasma and plasma concentrates are usually in a suitable state for applying to the column.

The pH can be adjusted by adding an aqueous solution of compounds which will buffer the pH of the resulting solution to within the desired range of 6.0 to 8.0, and which do not disturb the activity of the Factor VIII:C. Many such solutions are known to the skilled practitioner. One example is a buffer solution containing 20 mM imidazole and 0.1M lysine. Another example is 10 mM histidine and 0.1M glycine.

Referring to step (c), a neutral salt, such as calcium chloride, in amounts sufficient to make the solution of the starting material about 0.1 to 2M is added to provide for conductivity between 25 mS/cm and 500 mS/cm (milli-Siemens per cm). It is generally known that this conductivity range at neutral pH provides dissociation of Factor VIII:C from other plasma proteins.

The adsorbent materials employed in the column is a hydrophobic interaction matrix, such as pentyl agarose, hexyl agarose, phenyl agarose and the like. A suitable phenyl agarose is avaialble commercially under the trade name "Phenyl Sepharose", sold by Pharmacia Fine Chemicals Co.

The surface active agent (oxy-1,2-ethanediyl)$_{20}$ monododecanoate sorbitan (Polysorbate 20) or its analogs such as (oxy-1,2-ethanediyl)$_{20}$ monohexadecanoate sorbitan (Polysorbate 40), (oxy-1, 2-ethanediyl)$_{20}$ monooctadecanoate sorbitan (Polysorbate 60) and (oxy-1,2-ethanediyl)$_{20}$ mono-9-octadecanoate sorbitan (Polysorbate 80) were found to be effective for eluting Factor VIII:C from the hydrophobic interaction matrix. Similarly, good result was obtained with: α[4-1,1,3,3-(tetramethylbutyl)phenyl]- ω-hydroxy (oxy-1,2-ethanediyl)$_{100}$ which is sold commercially as TritonX100 ®·, $C_{10}$-$C_{16}$ and steroid analogs of N-dodecyl-N, N-dimethyl-3-ammonio-1-propanesulfonate; and derivatives of cholic acid, such as taurocholic acid and glycocholic acid.

In purifying Factor VIII:C, the hydrophobic adsorbent is first equilibrated to have a pH of about 6.0 to 8.0 by washing with a buffer having a pH of 6.0 to 8.0. It is also important that the ratio of Factor VIII:C to adsorbent materials does not exceed the capacity of the adsorbent materials, which is a value easily determined by those skilled in the technique of chromatographic separations. Generally, the capacity is 5 to 10 Factor VIII:C units per gram of wet resin when cryoprecipitate is used and higher when more purified source material is used. The adsorption process can be carried out in a batch mode or in a chromatographic column, using techniques and equipment customary in this field of technology.

The Factor VIII:C containing source material, which has also been adjusted to pH 6.0 to 8.0 and to which calcium chloride was added to make the solution 0.1 to 2M, is applied to the adsorbent allowing sufficient contact time for the desired protein-adsorbent interactions to occur.

Removal of foreign proteins is accomplished by washing the column with an aqueous buffer solution containing 0.1 to 0.5M $CaCl_2$ and 0.1 to 40% w/w ethylene glycol.

Further washing to remove residual contaminating proteins and Factor VIII:R is accomplished with an aqueous buffer containing 0.01 to 0.6M NaCl, 0.01 to 0.2M glycine, 0.001 to 0.020 $CaCl_2$ and 0.001 to 0.020 histidine.

Elution of Factor VIII:C is accomplished by adding 0.1 to 1% w/w of one of the aforementioned surface active agents to the above-described buffer solution after washing of contaminating protein and Factor VIII:R is completed. Alternatively, the buffer solution is made up to contain the surface active agents and then used to desorb the Factor VIII:C from the hydrophobic matrix of the column.

The eluate so collected yields a solution having a Factor VIII:C potency of 10 to 50 Units per ml. The collected eluate can be sterile filtered per se and used as an infusable formulation for therapeutic purposes or can be further processed as a source of Factor VIII:C. Alternatively, the solution may be sterile filtered and lyophilized for storage prior to therapy.

The invention will be illustrated by the following examples.

EXAMPLE 1

AHF activity was recovered from frozen human plasma as a cryoprecipitate at 0° C. using conventional techniques. The precipitate (20 g) was suspended in 60 ml of aqueous buffer at pH 6.9, clarified by centrifugation and purified by the immunosorbant technique as described by Zimmerman (U.S. Pat. No. 4,361,509). The resultant solution (200 ml) with a specific activity of 500 AHF Units per mg contained 400 Units AHF, 0.5M $CaCl_2$, 0.1M lysine, 0.02M histidine, 0.15M NaCl and 200 ng/ml of mouse protein as a result of leeching from the immunosorbent matrix. Three grams of phenylagarose were added to the solution and the matrix was collected in a 1.5×2 cm column. The supernate solution contained 90 Units AHF. 65% of the activity (200 Units) was recovered in 10 ml by elution with a buffer containing 0.6M NaCl, 0.01M $CaCl_2$, 0.01M histidine and 0.5% Polysorbate 20 at pH 6.8. In addition to a 10 fold concentration of the potency, 95% of the mouse protein was removed and the specific activity increased to 750 U/mg.

EXAMPLE 2

Antihemophilic activity was purified to 500 U/mg as in Example 1. It was then purified to 700 U/mg with the use of an aminohexyl column as described by Zimmerman (referred to in Example 1). The resultant material contained 700 Units AHF, 0.5M $CaCl_2$, 0.02M histidine, 0.1M lysine and 20 ng/ml mouse protein at pH 7.0. It was passed over a 1.5×2 cm column of hexylagarose and eluted sequentially: first with aqueous 0.5M $CaCl_2$; then 0.25M $CaCl_2$ in 25% ethylene glycol to remove mouse protein; then with 0.5% Polysorbate 20 to elute 410 Units of AHF activity as in example 1. Of the 40 ng mouse protein applied to the hexyl agarose as a contaminant, 28 ng was washed out with $CaCl_2$ and ethyleneglycol, while 13 ng was recovered with the product having a specific activity of 850 U/mg.

EXAMPLE 3

Purified AHF was obtained as in Example 1, except 760 Units was recovered from the immunosorbent column in the presence of 0.25M $CaCl_2$, 0.1M lysine, 0.02M histidine and 0.15M NaCl at pH 7.2. The specific activity increased from 1000 U/mg to 1400 U/mg by chromatography over a 1.5×2 cm column of hexyl agarose. The bound activity was first washed with the 0.25M $CaCl_2$ solution then 400 units was recovered in 10 ml by elution with 0.2% Triton X100 in the presence of 0.3M NaCl, 0.01M histidine and 0.001M $CaCl_2$ at pH 7.2.

EXAMPLE 4

The purified AHF, obtained as in Example 2, was passed through a 1×8 cm column of phenyl agarose. A total of 810 Units AHF and 80 ng mouse protein was then washed with 0.5M $CaCl_2$ followed by 40% ethylene glycol containing 0.25M $CaCl_2$. 68% of the residual mouse protein was removed in these first two washes. The AHF activity, 540 Units, and 20 ng mouse protein was recovered by elution with 0.5% Polysorbate 80 in the presence of 0.6M NaCl, 0.005M histidine and 0.002M $CaCl_2$ at pH 7.0. The specific activity was increased from 850 to 1200 U/mg.

EXAMPLE 5

A larger scale example employed 1465 Units AHF which had been purified from 50 grams cryopercipitate as in Example 2. The aqueous solution of AHF was applied to a 1×8 cm column of phenyl agarose and washed with 50 ml buffer containing 0.25M $CaCl_2$ and 0.01M histidine at pH 7.0. The activity, 970 Units, was then eluted with 66% yield by passage of a buffer containing 0.2% Polysorbate 80, 0.3M NaCl, 0.001M histidine and 0.002M $CaCl_2$ at pH 7.0. The final specific activity was 1800 U/mg.

Recovery, illustrating the result of the present invention, is shown in Table I.

TABLE I
PHENYL SEPHAROSE CHROMATOGRAPHY OF MONOCLONAL ANTI-VW PURIFIED VIII:C

| FORMU-LATION | COLUMN (CM) | LOAD (UNITS) | NON-BOUND (UNITS) | RECOVERY (UNITS) |
|---|---|---|---|---|
| Formula A | 1.5 × 2 | 400 | 90 | 200 (65%) |
| Formula B | 1 × 8 | 810 | 40 | 540 (70%) |
| Formula C | 1 × 8 | 1465 | — | 970 (66%) |

Formula A consists of 0.6M NaCl, 0.01 $CaCl_2$ and 0.01 histidine adjusted to pH 6.8 and 0.5% w/w (oxy-1,2-ethanediyl)$_{20}$ - monododecanoate sorbitan.

Formula B consists of 0.6M NaCl, 0.005M histidine, 0.002M $CaCl_2$ adjusted to pH 7.0 and 0.5% w/w (oxy-1,2-ethanediyl)$_{20}$ mono-9-octadecanoate sorbitan.

Formula C consists of 0.3M NaCl, 0.001M histidine, 0.002M $CaCl_2$ adjusted to pH 7.0 and 0.2% w/w (oxy-1,2-ethanediyl)$_{20}$ mono-9-octadecanoate sorbitan.

What is claimed is:

1. In a process for separating Factor VIII:C from a source material containing Factor VIII:C, Factor VIII:R and other plasma proteins, having the steps of
   (a) absorbing a Factor VIII:C/VIII:R and foreign protein complex from a plasma or commercial concentrate source onto particles bound to a monoclonal antibody specific for Factor VIII:R;
   (b) eluting Factor VIII:C, residual Factor VIII:R and foreign proteins with a saline solution;
   (c) adjusting the pH of the solution obtained in step (b) to about 6.0 to 8.0;
   (d) adding calcium chloride to make said solution about 0.1 to 2M;
   wherein the improvement comprises:
   (e) adsorbing Factor VIII:C, Factor VIII:R and foreign proteins from said solution onto a hydrophobic interaction matrix selected from the group consisting of pentyl agarose, hexyl agarose, heptyl agarose, octyl agarose and phenyl agarose;
   (f) eluting Factor VIII:R and foreign proteins from said hydrophobic interaction matrix by washing with an aqueous solution, having a pH of about 6.0 to 8.0, containing 0.1 to 0.5M $CaCl_2$ and 0.1 to 40% w/w ethylene glycol;
   (g) further washing the hydrophobic interaction matrix with a buffer solution, having a pH of 6.5 to 7.2, containing 0.01 to 0.6M NaCl, 0.01 to 0.2M glycine, 0.001 to 0.020M $CaCl_2$ and 0.001 to 0.020M histidine; and
   (h) eluting Factor VIII:C by washing with a water solution of 0.1 to 1% w/w of a surface active agent selected from the group consisting of (oxy-1,2-ethanediyl)$_{20}$ monododecanoate sorbitan, (oxy-1,2-ethanediyl)$_{20}$ monooctadecanoate sorbitan, (oxy-1,2-ethanediyl)$_{20}$ mono-9-octadecanoate sorbitan, a[4-1,1,3,3-(tetramethylbutyl) phenyl]-w-hydroxy (oxy-1,2-ethanediyl)$_{100}$, taurochloric acid, glycocholic acid, $C_{10}$–$C_{16}$ analogs of N-dodecyl-N, N-dimethyl-3-ammonio-1-propanesulfonate, and steroid analogs of N-dodecyl-N, N-dimethyl-3-ammonio-1-propanesulfonate.

2. The process of claim 1 wherein said source material is plasma containing AHF.

3. The process of claim 1 wherein said source material is a plasma concentrate containing AHF.

4. The process of claim 1 wherein said source material is a cryoprecipitate containing AHF.

5. The process of claim 1 wherein Factor VIII:C is eluted with an aqueous buffer solution containing 0.01 to 0.6M NaCl, 0.01 to 0.2M glycine, 0.001 to 0.020M $CaCl_2$, 0.001 to 0.020M histidine and 0.1 to 1% w/w of a surface active agent selected from the group consisting of (oxy-1,2-ethanediyl)$_{20}$ monododecanoate sorbitan, (oxy-1,2-ethanediyl)$_{20}$ monohexadecanoate sorbitan, (oxy-1,2-ethanediyl)$_{20}$ monooctadecanoate sorbitan, (oxy-1,2-ethanediyl)$_{20}$ mono-9-octadecanoate sorbitan, a[4-1,1,3,3-(tetramethylbutyl) phenyl]-w-hydroxy (oxy-1,2-ethanediyl)$_{100}$, taurocholic acid, glycocholic acid, $C_{10}$–$C_{16}$ analogs of N-docecyl-N, N-dimethyl-3-ammonion-1-propanesulfonate, and steroid analogs of N-dodecyl-N, N-dimethyl-3-ammonio-1-propanesulfonate.

* * * * *